(12) United States Patent
Webber et al.

(10) Patent No.: US 10,288,536 B2
(45) Date of Patent: May 14, 2019

(54) HISTOLOGY CASSETTE STACK

(71) Applicant: CellPath Ltd., Powys (GB)

(72) Inventors: Paul Webber, Powys (GB); Philip Webber, Powys (GB); Richard Titcombe, Powys (GB)

(73) Assignee: Cellpath Ltd., Newtown, Powys (GB)

( * ) Notice: Subject to any disclaimer, the term of this patent is extended or adjusted under 35 U.S.C. 154(b) by 0 days.

(21) Appl. No.: 14/632,723

(22) Filed: Feb. 26, 2015

(65) Prior Publication Data

US 2015/0241325 A1   Aug. 27, 2015

(30) Foreign Application Priority Data

Feb. 26, 2014 (GB) .................................. 1403380.7

(51) Int. Cl.
| | |
|---|---|
| *G01N 35/04* | (2006.01) |
| *G01N 1/36* | (2006.01) |
| *B01L 9/00* | (2006.01) |
| *G01N 1/31* | (2006.01) |
| *G01N 35/00* | (2006.01) |

(52) U.S. Cl.
CPC .................. *G01N 1/36* (2013.01); *B01L 9/52* (2013.01); *G01N 1/31* (2013.01); *G01N 1/312* (2013.01); *B01L 2200/025* (2013.01); *B01L 2300/021* (2013.01); *B01L 2300/043* (2013.01); *B01L 2300/0809* (2013.01); *B01L 2300/0812* (2013.01); *B01L 2300/0822* (2013.01); *G01N 2001/366* (2013.01); *G01N 2035/00861* (2013.01); *G01N 2035/0425* (2013.01)

(58) Field of Classification Search
CPC ............. G01N 1/36; G01N 1/31; G01N 1/312
USPC ......................................................... 221/307
See application file for complete search history.

(56) References Cited

U.S. PATENT DOCUMENTS

| | | | | |
|---|---|---|---|---|
| 1,562,196 A | * | 11/1925 | Abrams ................... | B65G 7/12 |
| | | | | 206/493 |
| 2,939,147 A | * | 6/1960 | Jacobson ............... | A47H 13/04 |
| | | | | 206/338 |

(Continued)

FOREIGN PATENT DOCUMENTS

| | | | | |
|---|---|---|---|---|
| EP | 1 077 179 | | 2/2001 | |
| EP | 1077179 A1 | * | 2/2001 | ............... B65D 1/34 |

(Continued)

OTHER PUBLICATIONS

The Extended European Search Report dated Jul. 14, 2015, for EP Application No. 15156674.2.

*Primary Examiner* — Rakesh Kumar
(74) *Attorney, Agent, or Firm* — Cook Alex Ltd.

(57) ABSTRACT

A histology processing cassette stack having a plurality of cassettes for use in analyzing or processing biological samples is disclosed. The stack of cassettes are arranged in register and threaded on a connecting strip which passes through an aperture in a direction perpendicular to the plane of the cassette though a front wall of the cassette. The cassettes are held in fixed relation and may be transported and inserted en bloc into a magazine in a printing system by the connecting strip having a retaining part abutting the bottom cassette and able to bear the weight of the stack of cassettes when suspended. A printing system comprising a housing having a void for receiving a magazine loaded with the stack of cassettes is also disclosed.

12 Claims, 7 Drawing Sheets

(56) References Cited

U.S. PATENT DOCUMENTS

| | | | | | |
|---|---|---|---|---|---|
| 3,180,489 | A * | 4/1965 | McGinn | ................ | B65D 71/00 |
| | | | | | 206/340 |
| 4,300,684 | A * | 11/1981 | Smith | .................... | E04F 21/28 |
| | | | | | 206/338 |
| 4,997,100 | A * | 3/1991 | Dudek | ................ | B65D 43/162 |
| | | | | | 220/784 |
| 5,163,580 | A * | 11/1992 | Beach | .................... | B65B 15/00 |
| | | | | | 206/445 |
| 5,865,341 | A * | 2/1999 | Martin | ................. | B23K 9/202 |
| | | | | | 221/197 |
| 6,176,383 | B1 * | 1/2001 | Lafond | ................... | B65D 1/34 |
| | | | | | 206/499 |
| 8,505,772 | B2 * | 8/2013 | Martin | .................... | A47F 1/10 |
| | | | | | 206/155 |
| 2002/0125166 | A1 * | 9/2002 | Laudat | .................... | B01L 9/52 |
| | | | | | 206/460 |
| 2005/0152809 | A1 * | 7/2005 | Hunnell | .................. | B01L 9/52 |
| | | | | | 422/537 |
| 2010/0194010 | A1 * | 8/2010 | Hughes | ................. | B01L 99/00 |
| | | | | | 269/10 |
| 2013/0224088 | A1 * | 8/2013 | Britz | ....................... | B41J 3/407 |
| | | | | | 422/554 |
| 2015/0241325 | A1 * | 8/2015 | Webber | ................ | G01N 1/312 |
| | | | | | 221/307 |

FOREIGN PATENT DOCUMENTS

| | | | | |
|---|---|---|---|---|
| EP | 1 238 706 | 9/2002 | | |
| EP | 2 881 175 | 6/2015 | | |
| EP | 2881175 A1 * | 6/2015 | ............... | B01L 9/52 |
| GB | 2 235 163 | 2/1991 | | |

* cited by examiner

HISTOLOGY CASSETTE STACK

This invention relates to a histology processing cassette stack and to a printing system adapted to receive the cassette stack.

Biological materials for histological examination are processed in large quantities for a wide range of diagnostic purposes. Tissue samples are prepared typically by a process involving embedding the tissue sample in paraffin or wax and slicing the embedded sample very thinly using a microtome. Prior to embedding the sample, it is typically processed using solutions selected according to the nature of the sample. The sample may be fixed, dehydrated, cleared, infiltrated with molten paraffin and optionally stained. Processing in which the sample is contacted with a processing solution and contacted with paraffin and may take place over an extended period, for example overnight. Typically, a large number of samples, for example around 300, can be processed together. The processing usually involves placing the material in a small box-like plastics carrier, known in the art as a "cassette".

Known cassettes for processing biological tissues typically comprise an open-topped box with a bottom wall through which processing materials or radiation for sample analysis may pass. The box may have a top cover which is moveable relative to the box and which may be detachable from the box. The cassette typically has two vertical side walls, a rear wall and a fourth wall, on the front side of the cassette which is typically sloping and includes an area for labelling the cassette. Known processing cassettes are described in, for example, GB-A-1230913 and U.S. Pat. No. 3,674,396.

Known processing cassettes are used with the cover in place as a tissue processing capsule and with the cover removed for embedding a specimen in paraffin. The processing cassette defines a cavity or compartment, which may be closed with the use of a perforated lid into which the biological tissue is placed for processing. Generally, processing cassettes define one cavity and process one sample at a time, although cassettes having multiple cavities to allow processing of more than one sample are known. Processing cassettes are typically constructed of plastics material and the bottom face has perforations made in the plastic material or a mesh through which processing liquids and or radiation for analysis may pass.

In processing biological tissue samples, it is essential that the cassette be marked with a unique identifier so as to provide unique identification of the source of the sample, for example a patient. Cassettes are typically automatically marked using a machine which imparts a unique identifier, for example a 2-dimensional bar-code, on the front wall of the cassette for ease of observation. The marking suitably is indelibly applied to the cassette, for example, by printing onto or etching into the material from which the cassette is constructed.

Histology cassettes are generally of a "standard size" as it is required to fit in other apparatus, for example fit standard specimen holders of microtomes and in printing equipment, employed to label each cassette with information typically relating to the sample in the cassette for example, the patient from whom the sample has been taken. "Standard size" histology processing cassettes typically have internal dimensions of 28 to 32 mm×25 to 28 mm×5 to 6 mm. Minor variations in size may occur, dependent, for example, upon the wall thickness of the box. Whilst standard size cassettes may be employed for the majority of tissue samples, certain samples, for example prostate samples, are larger than the standard size cassette and require a larger cassette. Larger cassettes typically have an area four times that of a standard cassette and a depth of around twice that of a standard cassette, for example dimensions of around 50 to 55 by 70 to 80 by 5 to 16 mm are conventionally employed for use in processing larger samples.

Large numbers of cassettes may be processed simultaneously and automated labelling enables rapid throughput and with the unique identification data being stored electronically offers a failsafe system of ensuring the identifier on the cassette corresponds to the sample being processed in the cassette. The unique identifier is typically taken from electronically stored patient records, for example from a Laboratory Information Management System, so that patient data need be input in the system only once, and errors in manual labelling or transcription are avoided. Devices for applying a unique identifier to a cassette are known and may be adapted to receive cassettes of the standard size and represent a significant capital investment.

Cassettes typically may be packaged in bags and supplied as such for loading into a storage compartment or magazine in a printer or other apparatus. Manually loading cassettes individually into a printer device or a magazine for loading into the printing device however is laborious and time-consuming.

EP-A-1238706 addresses this problem by providing a stack of cassettes which are physically bound together by means of a weld seam or an adhesive tape so as to facilitate transportation and provide for simple charging of a printer device or magazine. However, the cassette stack must be subjected to a processing step to apply the weld seam or to apply an adhesive tape to the cassettes when oriented and stacked, and on use must be disconnected from the physical binding to the tape or the weld seam.

EP1077179 provides a collective stacked arrangement of cassettes using an interconnecting band, string or wire which passes through both vertical side walls of the cassette and the ends of which are connected to form a loop. Further, the cassettes shown in EP-A-1077179 comprise guide means for the interconnecting band, string or wire which may be at an angle and may be closed or open, in the form of a channel.

The cassettes must therefore be manufactured with a specific guiding means being included in the design. Standard cassettes in commercial use do not typically, in the vast majority of cases, include such means. The guide means in some cases may undesirably impinge on the shape and dimensions of the sample compartment. Where an open channel is employed, the band, string or wire may disadvantageously dislocate from the guide means upon withdrawal.

A further problem arises as the cassettes must remain in register once loaded to ensure smooth movement of the cassette through the holder or magazine. Manual loading may require adjustment of dislodged or unevenly stacked cassettes and this may be time-consuming. Manipulation of the cassettes or application of force to them, once loaded may cause one or more cassettes to alter its position relative to adjacent cassettes leading to complications as the cassettes pass through the magazine to the point of dispensing.

We have now devised a mechanism which ameliorates problems with known apparatus and methods and the problem of a labour intensive process of stacking cassettes manually and of applying a physical binding to connect the cassettes and disconnecting the cassettes from each other in use.

The invention provides in a first aspect a histology processing cassette stack comprising a plurality of histology processing cassettes adapted to receive a biological sample for analysis or processing, the cassettes being threaded on a connecting strip such that the cassettes are arranged in register wherein the cassettes have a bottom face comprising at least in part a sample support surface, two side walls, a back wall, a front wall and a top face, an aperture in the top face for receiving the connecting strip in a direction out of the plane of the cassette, for example in a generally perpendicular direction to the plane of the cassette wherein the connecting strip comprises a connecting part upon which the cassettes are threaded and a retaining part which abuts the bottom face of the bottom cassette in the stack.

Suitably, the stack of cassettes is insertable into a hopper, magazine or cassette stack in a printing system.

Suitably, the histology processing cassette comprises a sample compartment defined by the bottom face, the two side walls, the back wall and the front wall where the front wall comprises a inner front wall defining the sample compartment and an outer front wall wherein the inner front wall and the outer front wall define a cavity through which the connecting strip passes and the aperture is in the top face in register with the cavity.

The cassettes are thread on the connecting strip and the connecting strip is not bound to the cassettes, nor are the cassettes bound to each other in any manner. The connecting strip is not an adhesive tape. The cassettes are suitably movable relative to each other in that they may freely slide along the strip although once thread onto the strip, the cassettes will suitably be in contact with the adjacent cassettes so as to form a stack of cassettes.

The cassette is suitably of a conventional construction comprising a box for receiving a sample to be analysed or processed comprising a bottom face comprising at least in part a sample support surface, two side walls, a back wall and a front sloping wall and optionally a top face which may be open or closed. The cassette also include a front inner wall which together with the side walls, back wall and bottom face defines a sample compartment within which the sample to be analysed is located. Suitably the front inner wall is vertical and the front wall is sloping. The front inner wall and front wall with the forward parts of the two side suitably define a front cavity. The aperture is suitably located in the top side of the front part of the cassette such that the connecting strip passes through the aperture and into the cavity defined between front inner wall and front wall.

The aperture is suitably of similar dimensions to the cross section of the connecting strip such that the connecting strip slidably passes through the aperture snugly. The aperture is preferably in the form of a slot in the thickness of the material in the top face of the cassette. Suitably the slot acts to locate the connecting strip in a relatively fixed lateral relationship with the cassette such that there is minimal and preferably no lateral movement.

Preferably, the aperture is located in the top face of the cassette, forward of the sample compartment and is located so that the connecting strip passes through the cavity between the inner front wall and the front wall. In this way, the design of the cassette need not be altered from the conventional design, avoiding the need for redesign, retooling and also avoids the sample compartment being compromised to accommodate guide means which impinge into the space of the sample compartment. The connecting strip may accordingly pass through the aperture, within the outer periphery of the cassette but outside the inner periphery which defines the sample compartment.

The connecting strip suitably passes through only one aperture on each cassette so as to reduce the risk of fouling or dislodging any given cassette as the connecting strip is removed once the stack of cassettes has been loaded into the dispensing apparatus.

The connecting strip suitably may pass slidably and snugly through the aperture and so provides a guiding function to hold the cassette in a relatively fixed position with minimal and preferably no lateral movement as well as acting to retain the cassettes in general register.

Advantageously, each cassette comprises only one aperture for receiving the connecting strip. The aperture is suitably a closed aperture in that the aperture defines a continuous solid periphery through which the connecting strip passes. The connecting strip may only be removed by being passed through the aperture.

Suitably the connecting strip is a rigid tape, preferably made of a plastics material. The connecting strip preferably comprises a connecting part upon which the cassettes are threaded and a retaining part. The retaining part is preferably deformable and may be bent relative to the connecting part, for example, by bending the connecting strip to create a crease such that the retaining part extends under the bottom face of the bottom cassette and the connecting part links the cassettes together and maintains them in register in a fixed orientation. Suitably, the connecting strip has sufficient resilience that the retaining part and connecting part remain in a fixed relative position with the cassettes threaded on the connecting strip whilst the connecting part is suspended such that the retaining part is able to bear the weight of the stack of cassettes. In a preferred embodiment, the connecting strip is a creasable plastics tape. Where a cassette has a mass m and the number of cassettes in the stack is n, the retaining part is able to bear a weight of m×n×g, g being gravitational acceleration, in that the weight of the stack may be borne by the retaining part as the stack of cassettes is suspended so the stack remains intact during a loading operation and the retaining part of the connecting strip is sufficiently does not cause the retaining part to rotate relative to the connecting part such that the cassettes are unthreaded on the connecting strip.

By employing a single aperture, the present invention minimises the couple which may be applied to the cassette in withdrawal of the connecting strip. In EP-A-1077179, a strip passes through opposite side walls of a cassette. Upon withdrawal of the strip, pressure must be applied to the top of the stack of cassettes and one side may experience a downward frictional force and the opposite side an upward frictional force which, together apply a rotational couple to each cassette which is larger than that applied were a single aperture to be employed. This may cause a cassette to dislodge or otherwise move from being in register with adjacent cassettes.

Advantageously, as the present invention provides the aperture in the front wall of the cassette, any small degree of rotation is about a horizontal axis through the width of the cassette. If the front of the cassette is slightly lifted as the connecting strip is withdrawn upwardly, the bottom face and top face of adjacent cassettes slide relative to each other in a lengthways direction. There is less risk of the cassette becoming dislodged or out of register with its adjacent cassettes as compared to the case where the cassettes have apertures or guides in a side wall which may cause rotation about a lengthways axis so the bottom and top faces of adjacent cassettes slide along the narrower width.

The stack of cassettes may comprise as many or as few cassettes as desired and this will typically be determined according to the size of the magazine of the printing system to be employed to label the cassettes. Suitably the stack comprises at least 20 cassettes, preferably 30 to 50 cassettes, for example 40 cassettes.

Suitably, the cassettes are arranged one above the other when threaded on the connecting strip and may be inclined at an oblique angle to the connecting part of the connecting strip whereby a cassette is longitudinally offset to the adjacent cassette in that the side walls of adjacent cassettes are in register but the front and back walls of a cassette may be forwardly or backwardly displaced relative to the front and back walls of an adjacent cassette.

Where the stack is vertical the cassettes may be horizontal or inclined at an angle of up to 45 degrees, preferably 10 to 30 degrees, relative to the horizontal when located in the magazine.

The top face may be closed by an openable lid. Optionally the lid is pivotally mounted on the cassette. Suitably, the lid comprises a plastics sheet having perforations and engages releasably with the box of the cassette. Suitably, the lid is moveable relative to the box of the cassette. Preferably the lid is detachable and the lid and box have complementary engaging means, for example, recesses and lugs, to allow secure attachment of the lid to the box. If desired, the lid may be permanently attached to the box and pivotally mounted, for example, through a hinge, to the box.

Preferably the cassette is constructed of a plastics material as is the lid where applicable. Suitably these parts are constructed by injection moulding a thermoplastics material. Although some lids may be constructed with a stainless steel or other suitable material.

The bottom face, and where present, the top face or lid, may contain perforations, a mesh, or otherwise be transmissible to processing liquids and/or radiation for analysis.

The box may comprise a single compartment or multiple compartments. Preferably, the compartment is at least 5 mm wide in their smallest dimension parallel to the top or bottom face. Where multiple compartments are employed, the compartments may be any suitable shape, for example elongate and square, and may be arranged in any desired manner in the cassette. Preferably, the compartments are arranged to extend across the full width of the cassette. Endoscopy biopsies, for example, may be processed in compartments which are more square than elongate.

The cassette comprises an aperture for receiving the connecting strip in a direction perpendicular to the plane of the cassette. The aperture may be in the bottom face or within a side wall, end wall, or preferably the front wall of the cassette. The aperture allows the strip to pass through the cassette which is thereby threaded onto the strip and oriented generally at least 60 degrees and preferably generally at right angles to the strip. Suitably, the aperture and connecting strip are of a similar cross-section. The aperture and strip are preferably dimensioned such that there is a snug sliding fit so that the cassettes are freely movable along the strip whilst the risk of any skewing of the cassette so that adjacent cassettes are not in register is reduced. Preferably the aperture for receiving the connecting strip is separate from the sample compartment and preferably located at or towards the front side of the cassette so as to reduce the risk of contamination of the sample.

The front wall of the cassette is suitably adapted to receive information comprising a unique identifier for the biological sample applied automatically, for example, by a conventional printing system or device. The unique identifier may comprise alpha-numeric characters or some other form of marking, for example a bar-code.

The invention provides in a second aspect a printing system comprising a housing having a void for receiving a magazine loaded with a stack of cassettes according to the present invention, an outlet for dispensing single cassettes from the stack successively and printing means for applying information comprising a unique identifier to the front side of the cassette.

The present invention is further described by way of example only with reference to the accompanying drawings, in which.

Figure 1:
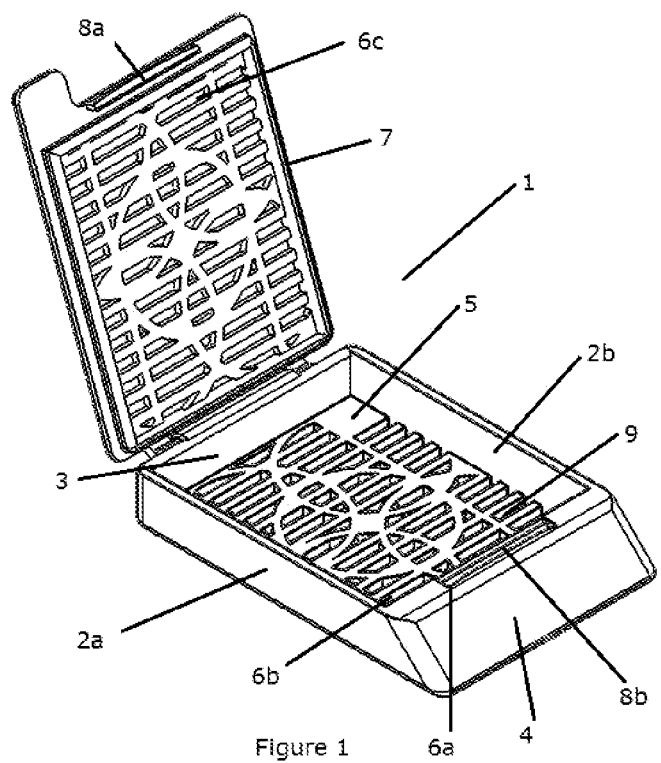
FIG. 1 shows in a perspective view a known histology processing cassette with a closable lid.

FIG. 1 shows a known histology processing cassette 1. Cassette 1 has side walls 2a, 2b, rear wall 3 and front wall 4 which define the periphery of the cassette 1 and a bottom face 5 defining the sample compartment. The front wall 4 is preferably sloping and adapted to receive a unique identifier to ensure that the source of the sample remains known. The cassette may also have partition walls within the sample compartment to provide for a multiplicity of sample compartments within a single cassette. The cassette has an aperture 6a or 6b and 6c for receiving a connecting strip in a direction generally perpendicular to the plane of the cassette 1. The aperture 6a is preferably located in the top side of the front wall of the cassette 1. Alternatively the aperture may be located in the bottom face 5 and, where a lid 7 is present a corresponding aperture 6c in register with aperture 6b in the bottom face 5 is located in the lid 4. The lid 7 may be removable from the cassette 1 or may be releasably closable employing complementary engaging parts 8a and 8b about hinge 8. The lid 7 may be using the releasable and aperture 6.

Figure 2:
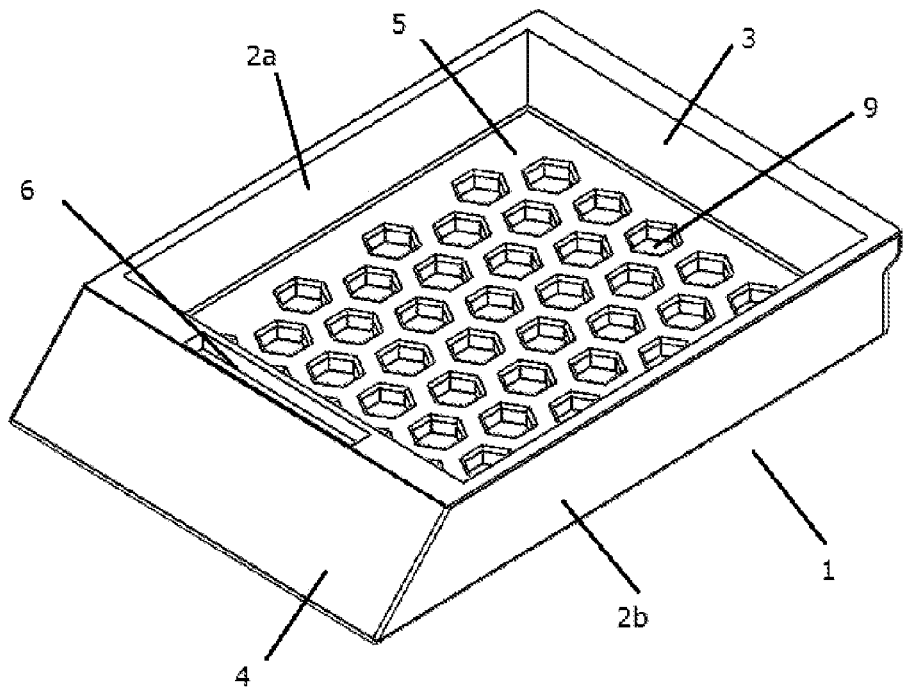
FIG. 2 shows in a perspective view a known histology processing cassette without a lid.

FIG. 2 shows a known histology processing cassette 1 without a top face.

In FIGS. 1 and 2, the bottom face of the cassette 1 has perforations 9 or may comprise a mesh. The cassette 1 is dimensioned and shaped so as to be loadable in and removable from a printing system or device. Any known cassettes having an aperture 6 or other known cassettes modified in design to have an aperture 6 may be employed in the present invention.

Figure 3:
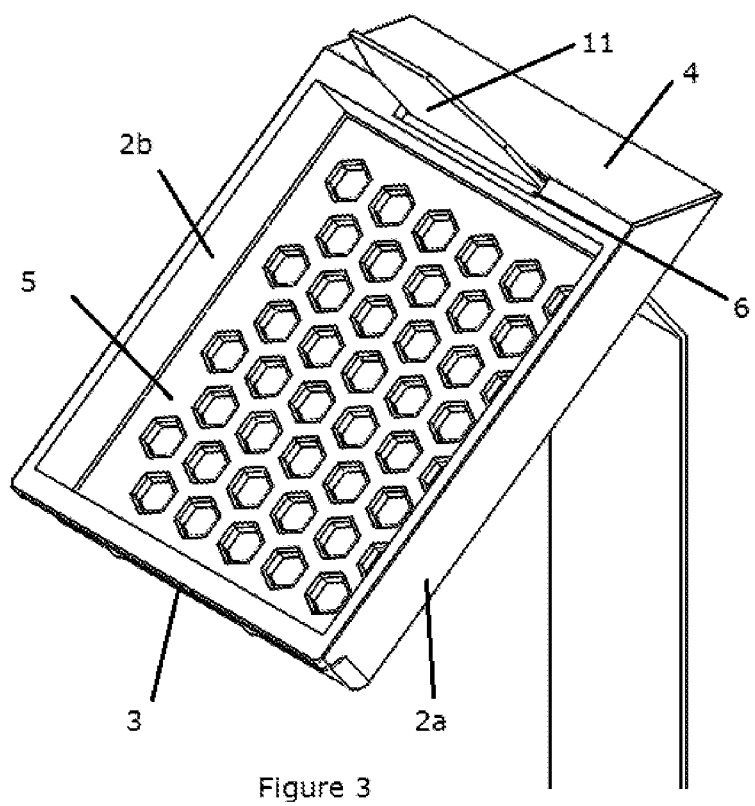
FIG. 3 shows in a perspective view a histology cassette being threaded onto a connecting strip.

FIG. 3 shows a cassette 1 which is being threaded on a connecting strip 11. The walls 2a, 2b, 3 and front inner wall 10 together with bottom face 5 define the sample compartment within which the sample to be analysed is located. Front inner wall 10 and front wall 4 with the forward parts of walls 2a and 2b suitably define a front cavity 17 (shown in FIGS. 6 and 7) between front inner wall 10 and front wall 4. The aperture 6 is suitably located in the top side of the front part of the cassette such that the connecting strip passes through the aperture 6 and into the cavity 17 defined between front inner wall 10 and front wall 4.

The aperture 6 is suitably of similar dimensions to the cross section of the connecting strip 11 such that the connecting strip 11 slidably passes through the aperture 6 snugly and so provides a guiding function to hold the cassette in a relatively fixed position with minimal and preferably no lateral movement.

Figure 4:
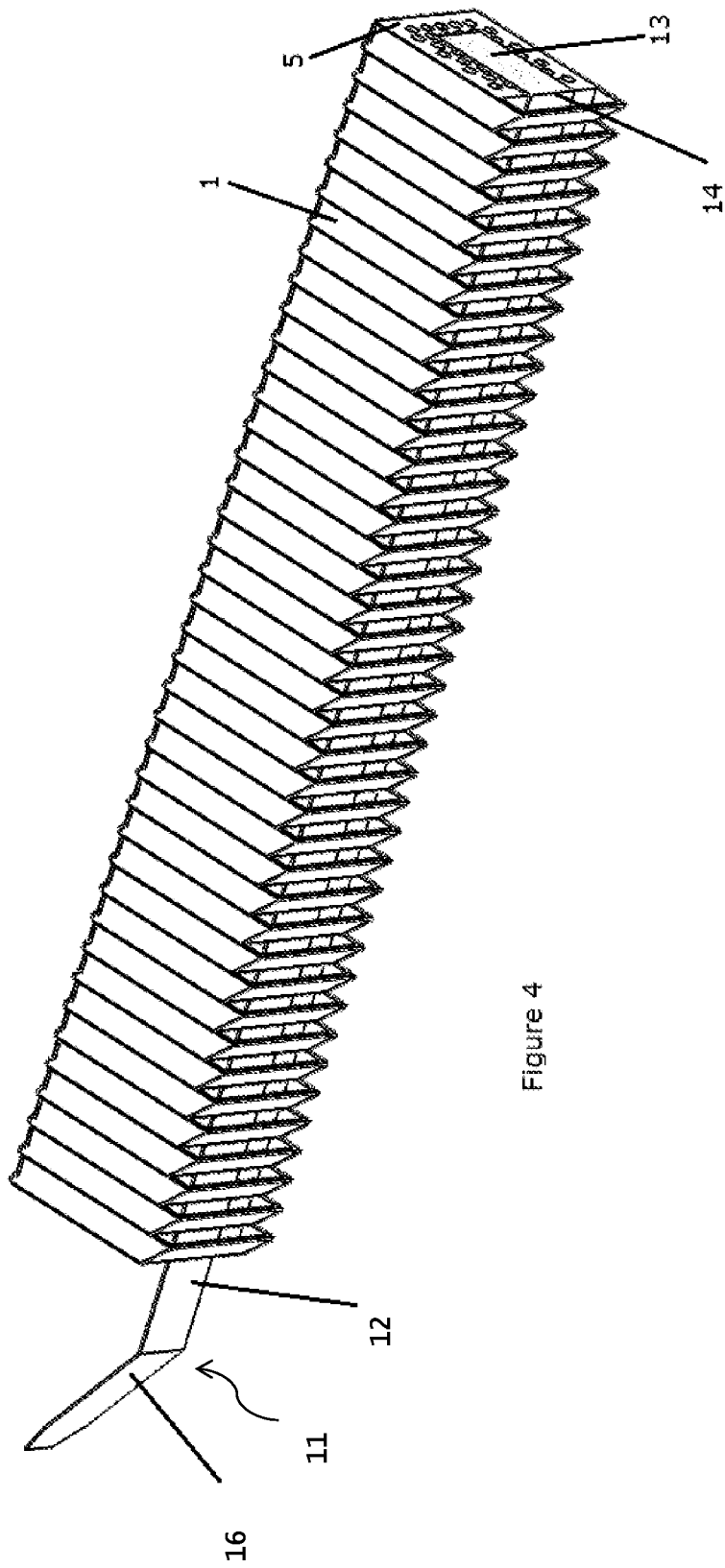
FIG. 4 shows in a perspective view a histology processing cassette stack according to the invention.

FIG. 4 shows a plurality of cassettes 1 threaded on a connecting strip 11 which has a connecting part 12 and a retaining part 13 to form a stack of cassettes according to the invention. The connecting strip also includes an end 16 for gripping the connecting strip 11. The retaining part 13 abuts the bottom face 5 of the bottom cassette 1' and has been bent relative to the connecting part 8. A crease 14 is present in the connecting strip 11. The cassettes are all maintained in register as the aperture 6 is approximately the same cross-sectional shape as the connecting strip 11.

Figure 5:
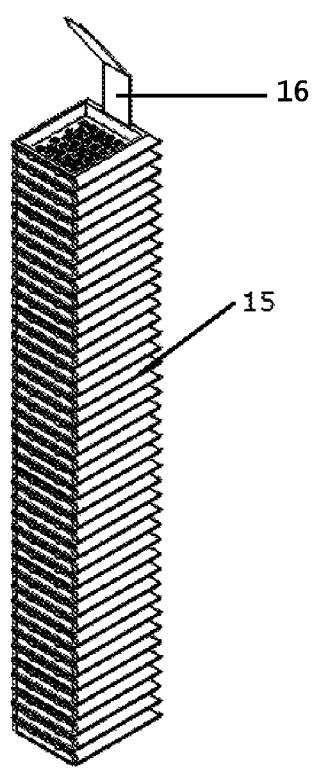
FIG. 5 shows in a perspective view a histology processing cassette stack according to the invention being suspended.

FIG. 5 shows a stack of cassettes 15 according to the invention suspended by holding the end 16 of the connecting part 12 and the retaining part 13 abutting the bottom face 5 of the bottom cassette 1' of the stack of cassettes retains all the cassettes on the connecting part 12. The weight of the stack of cassettes is being borne by the retaining part 13 and the connecting strip 11 is constructed of a plastics material such that it has sufficient resilience to bear this weight.

Figure 6:
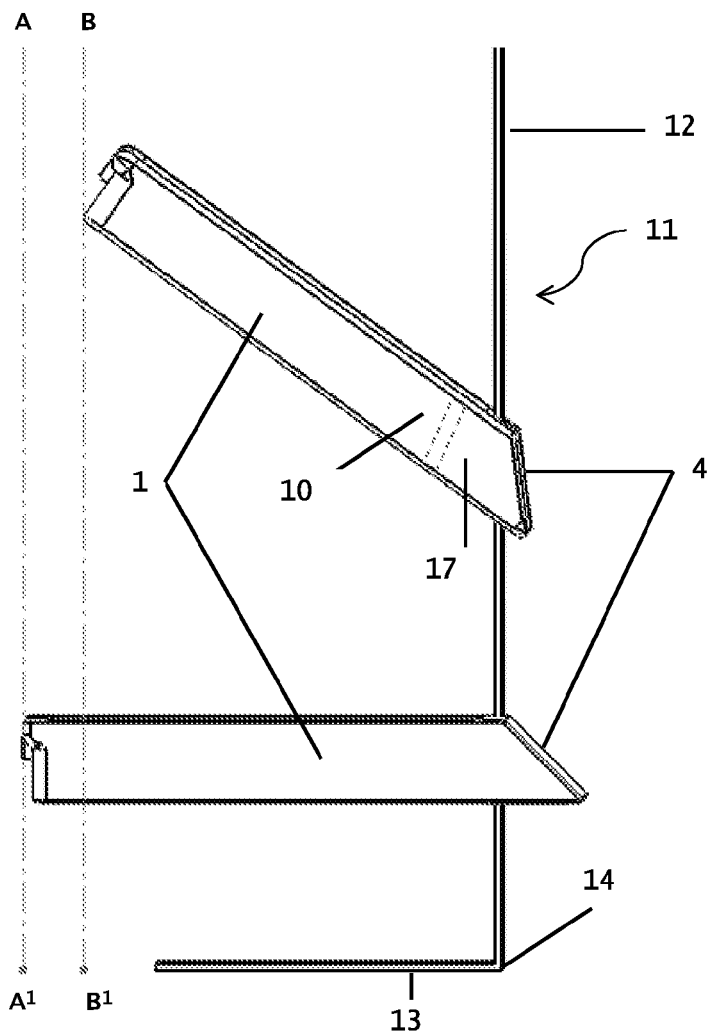
FIG. 6 shows a side view of a two cassettes threaded onto a connecting strip.
Figure 7:
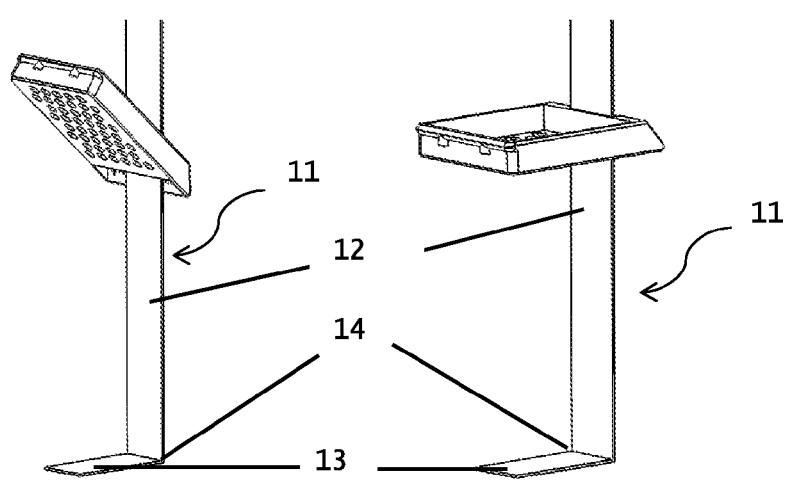
FIG. 7 shows a perspective view of FIG. 6.

FIGS. 6 and 7 show two cassettes 1 mounted on the connecting strip 11 with one inclined at an angle of about 45 degrees to the horizontal and the other shown in a horizontal position. The front inner wall is shown in dashed lines. Where the cassette is in the inclined position, the connecting part 12 passes through the aperture 6 and abuts the reverse side of wall 4, labelled as 4' in FIG. 8. In the horizontal position, the connecting strip 12 abuts the reverse side of wall 10.

Figure 8:
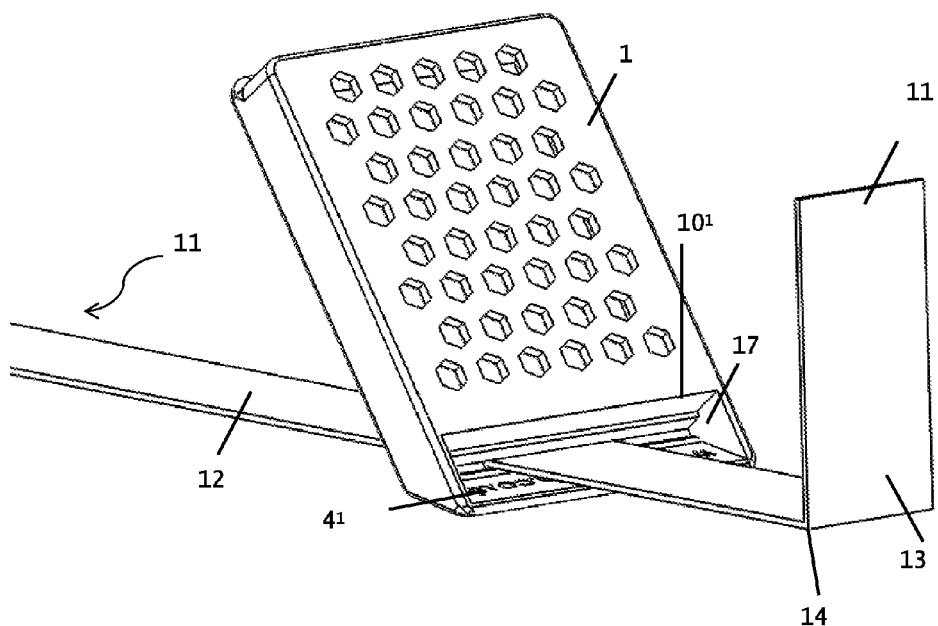
FIG. 8 shows a perspective view from the bottom side of a cassette threaded onto a connecting strip.
Figure 9:
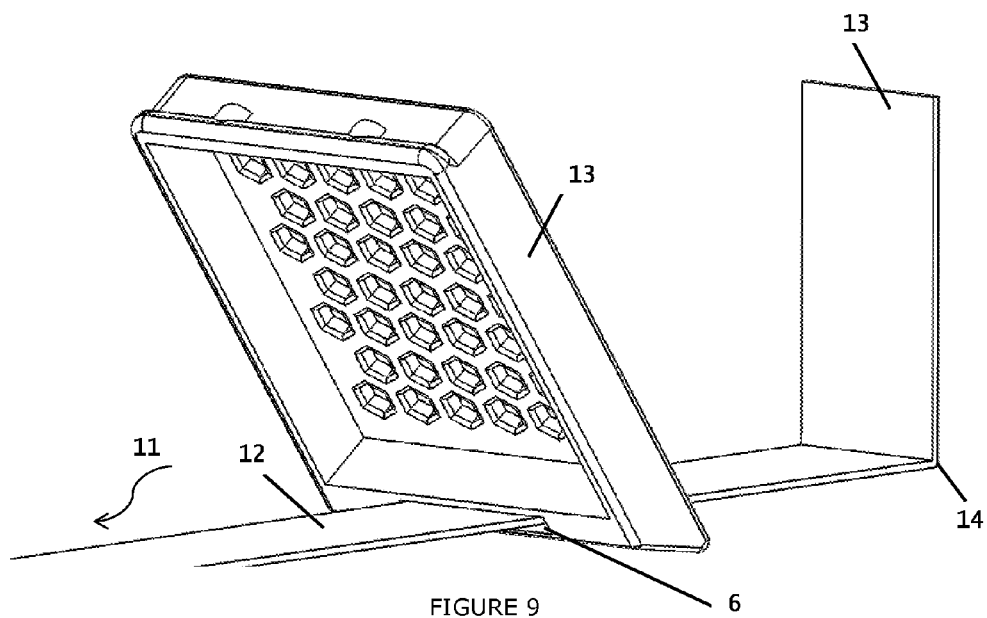
FIG. 9 shows a perspective view from the top side bottom of a cassette threaded onto a connecting strip.

When the cassette is in the inclined position, the horizontal distance front the front edge of the cassette at the bottom of front wall 4 to a vertical plane passing though line B-B' perpendicular to the plane of the page at the most rearward part of the cassette 1 is significantly shorter than the corresponding distance to vertical plane passing through line A-A' when the cassette 1 is horizontal. For a standard sized cassette, the distance from the front of wall 4 to plane B-B' when the cassette is inclined at about 45 degrees is about 33 mm and from the bottom of wall 4 to plane A-A', when horizontal, about 41 mm. The hopper 20, shown in FIG. 10 may therefore be of shorter length if the cassette stack 15 is loaded with the cassettes at 45 degrees FIGS. 8 and 9 show cassette 1 mounted on the connecting strip 11 inclined at an angle of about 45 degrees to the horizontal and showing the reverse side of front inner wall 10, denoted as 10', and the reverse side of front wall 4, denoted as 4' which together with a portion of the side walls define cavity 17.

Figure 10:
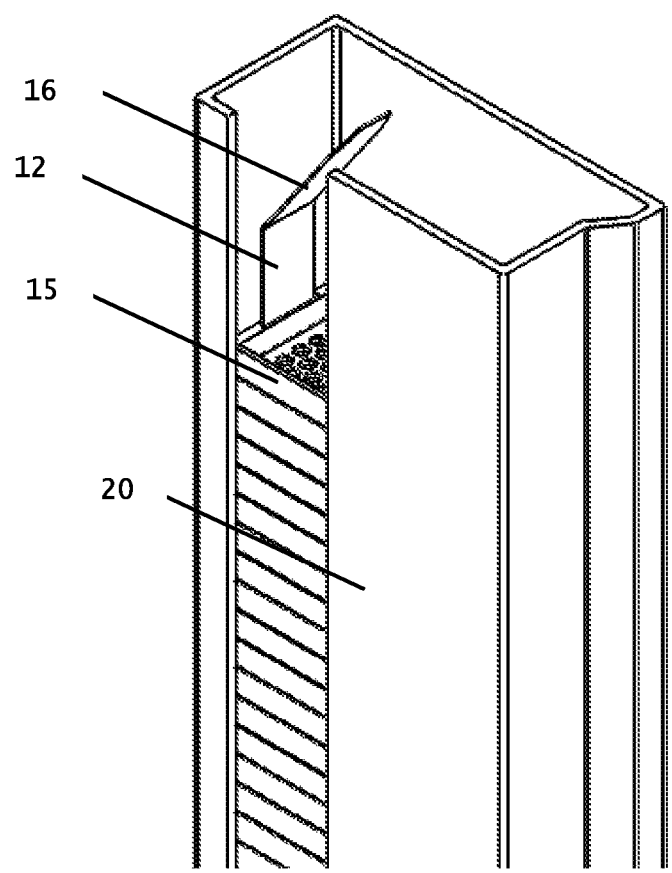
FIG. 10 shows in a perspective view a histology processing cassette stack according to the invention located in a hopper, cassette holder or magazine.

FIG. 10 shows the stack of cassettes 15 loaded into a hopper 20. The connecting strip 11 may be removed manually or by automated means by gripping end 16 and withdrawing the connecting strip upwardly in a manner such as not to dislodge the alignment of any individual cassette.

The invention claimed is:

1. A histology processing cassette stack configured for insertion into a magazine in a printing system, said stack comprising a plurality of histology processing cassettes adapted to receive a biological sample for analysis or processing, the cassettes being threaded on a non-adhesive connecting strip, the connecting strip being a rigid tape, such that the cassettes are arranged in register wherein the cassettes have a bottom face comprising at least in part a sample support surface, two side walls, a back wall and a front wall and a top face and an aperture in the form of a slot in the top face for receiving the connecting strip in a generally perpendicular direction to a plane of the cassette and a plane of the side walls wherein the connecting strip comprises a connecting part upon which the cassettes are threaded and a retaining part which abuts the bottom cassette in the stack wherein the connecting strip and the aperture in the cassette have the same cross-sectional shape and are dimensioned such that there is a snug sliding fit so that the cassettes are freely movable along the strip and do not move laterally of the strip to a material extent, and wherein the cassettes are not adhered to the strip.

2. A histology processing cassette stack according to claim 1 wherein the cassette comprises a sample compartment defined by the bottom face, the two side walls, the back wall and the front wall where the front wall comprises an inner front wall defining the sample compartment and an outer front wall wherein the inner front wall and outer front wall define a cavity through which the connecting strip passes and the aperture is in the top face in register with the cavity.

3. A histology processing cassette stack according to claim 1 wherein the connecting strip and the cassettes are not physically bound to each other.

4. The histology processing cassette of claim 1 wherein said retaining part abuts the surface of said bottom face of said bottom cassette that is opposite of said sample support surface.

5. A histology processing cassette stack according to claim 1 wherein the connecting strip is deformable such that the retaining part may be bent relative to the connecting part.

6. A histology processing cassette stack according to claim 1 wherein the cassette stack comprises a weight and the connecting strip has sufficient resilience that the retaining part and connecting part remain in a fixed relative position with the cassettes threaded on the connecting strip whilst the connecting part is suspended such that the retaining part bears the weight of said cassette stack.

7. A histology processing cassette stack according to claim 1 wherein the connecting strip is a creasable tape.

8. A histology processing cassette stack according to claim 1 wherein the front wall is adapted to receive information comprising a unique identifier for the biological sample applied automatically.

9. A histology processing cassette stack according to claim 1 wherein the aperture for receiving the connecting strip is separate from the sample compartment in the cassette.

10. A histology processing cassette stack according to claim 1 wherein the cassette comprises one and only one aperture for receiving the connecting strip.

11. A histology processing cassette stack according to claim 1 wherein the cassettes are arranged at an angle of up to 45 degrees to the horizontal when located in the magazine.

12. A histology processing cassette stack according to claim 1 wherein the top face of each cassette is open.

* * * * *